US010980561B1

United States Patent
Fahmy et al.

(10) Patent No.: US 10,980,561 B1
(45) Date of Patent: Apr. 20, 2021

(54) ROTARY RESECTOSCOPE

(71) Applicant: King Abdulaziz University, Jeddah (SA)

(72) Inventors: Omar A. Fahmy, Jeddah (SA); Nabil A. Alhakamy, Jeddah (SA); Osama A. Ahmed, Jeddah (SA); Usama A. Fahmy, Jeddah (SA); Shadab Md, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/997,082

(22) Filed: Aug. 19, 2020

(51) Int. Cl.
*A61B 17/32* (2006.01)
*A61B 1/307* (2006.01)
*A61B 17/42* (2006.01)
*A61B 1/31* (2006.01)

(52) U.S. Cl.
CPC ...... *A61B 17/320016* (2013.01); *A61B 1/307* (2013.01); *A61B 1/31* (2013.01); *A61B 17/42* (2013.01); *A61B 2017/4216* (2013.01)

(58) Field of Classification Search
CPC ... A61B 17/320016; A61B 1/31; A61B 17/42; A61B 2017/4216; A61B 17/32
See application file for complete search history.

(56) References Cited

U.S. PATENT DOCUMENTS

| | | | |
|---|---|---|---|
| 5,133,713 A | 7/1992 | Huang et al. | |
| 6,296,639 B1 | 10/2001 | Truckai et al. | |
| 6,676,658 B2 | 1/2004 | Burbank et al. | |
| 7,300,447 B2 | 11/2007 | Eliachar et al. | |
| 8,012,153 B2 | 9/2011 | Woloszko et al. | |
| 2008/0188711 A1* | 8/2008 | Eliachar .............. | A61B 18/149 600/106 |
| 2009/0062793 A1 | 3/2009 | Eliachar et al. | |
| 2010/0063353 A1 | 3/2010 | Eliachar et al. | |

OTHER PUBLICATIONS

Merriam-Webster definiton for "telescope"; https://www.merriam-webster.com/dictionary/telescope (accessed Nov. 19, 2020).*
Merriam-Webster defintion for "about"; https://www.merriam-webster.com/dictionary/about (accessed Nov. 19, 2020).*

* cited by examiner

*Primary Examiner* — Wade Miles
(74) *Attorney, Agent, or Firm* — W & C IP

(57) ABSTRACT

A rotary resectoscope is disclosed with a novel mechanism for endoscopic resection. Resection is performed by a rotary motion instead of the conventional linear motion. A novel resection loop and working element for controlling the movement of the resection loop allow the resection loop to move in clockwise and counterclockwise rotation. Embodiments include both monopolar and bipolar diathermy resectoscopes.

12 Claims, 6 Drawing Sheets

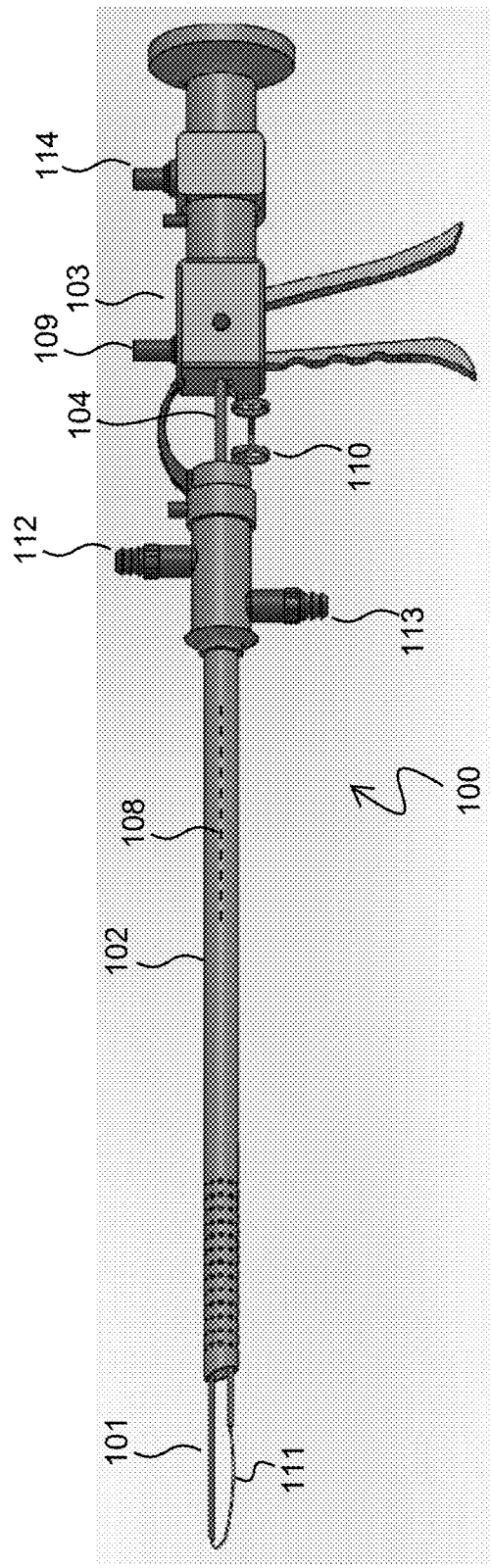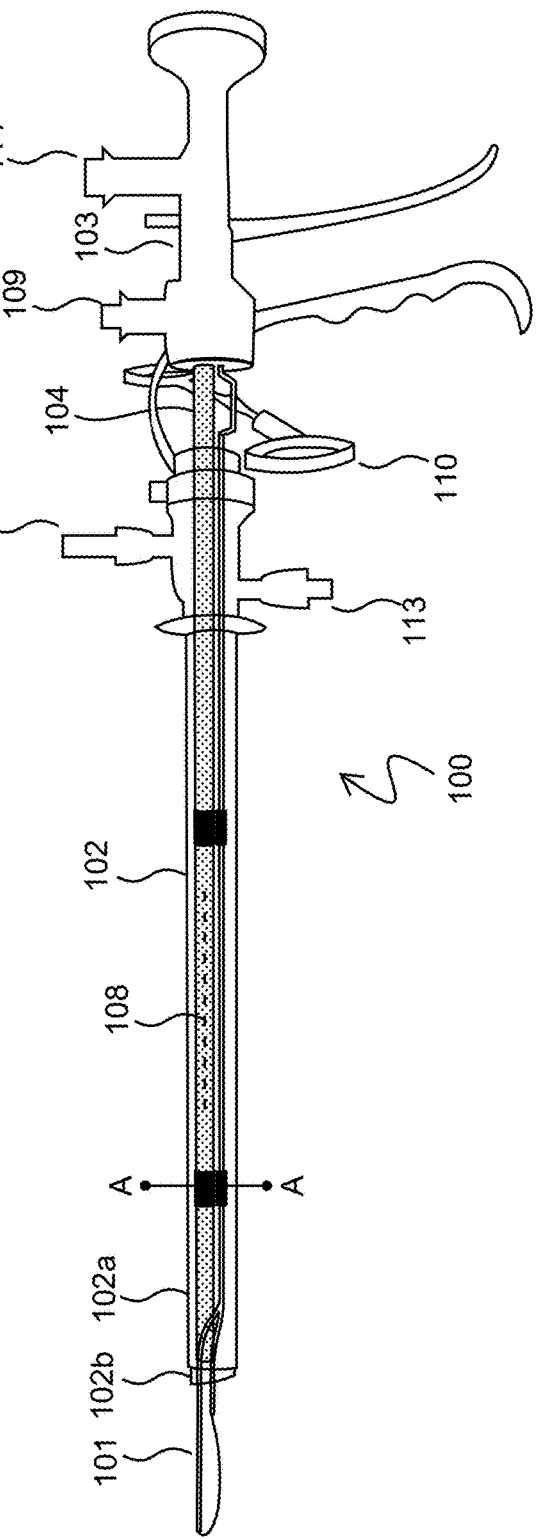
Figure 1
Figure 2

US 10,980,561 B1

ROTARY RESECTOSCOPE

FIELD OF THE INVENTION

Exemplary embodiments generally relate to resectoscopes and, in particular, the manner of control and resection performable with resectoscopes.

BACKGROUND

A resectoscope is an endoscopic instrument. One exemplary use of a resectoscope is to resect prostate or bladder lesions into small pieces of tissue under direct optical vision. A resectoscope's cutting mechanism uses electrical current that passes through a metal wire loop at the tip of the resectoscope. Resectoscopes were initially developed by Maximilian Stern (1877-1946), who performed the first transurethral resection of the prostate (TURP) in history in 1926. For many years up to the present day, transurethral resection has remained the standard surgical option for prostatic enlargement and for biopsy or resection of bladder tumors.

The mechanical aspect of the cutting action of a resectoscope is by moving the cutting loop against the tissue in a linear motion following the longitudinal axis of the resectoscope. This mechanical actuation is generally the same whether a resectoscope is monopolar or bipolar. Consistent with the linear mode of mechanical actuation, the maximum size of the cutting loop must be less than the internal diameter of the resectoscope sheath so the loop can be introduced and removed from the resectoscope sheath. As the resectoscope is introduced through the urethra, the external diameter cannot exceed certain limits.

FIGS. 10A, 10B, and 10C depict a conventional resectoscope 900 consistent with the preceding paragraph. The resectoscope 900 includes an electrode assembly 940 (FIG. 10C) of which a distal electrode tip 943 is visible, a sheath 902, a telescope tube 903, a spring-loaded link 904, a connector 905 to which a light source may be connected, and handles 906 and 907. The electrode assembly 940 comprises a support body 941, a spring clip 942, and a distal electrode tip 943. The spring clip 942 is configured to secure the electrode assembly 940 to the telescope tube 903. The spring clip 942 is semi-cylindrical in shape and fixedly connected to the support body 941. The spring clip 942 may be snapped on to the telescope 903 or, in the alternative, the telescope 903 may be passed through the spring clip 942. The resectoscope 900 is actuated with a linear motion parallel to the longitudinal axis of the resectoscope, as indicated by the arrows 921 in FIG. 10B. The dotted lines 922 show a linearly extended position of the distal electrode tip 943. The distal electrode tip 943 is configured as a loop which is extendable and retractable from the sheath 902 to perform tissue cutting operations. The loop is semi-circular and sized smaller than the diameter of the sheath 902.

SUMMARY

According to an exemplary aspect of some embodiments, a rotatory resectoscope is disclosed with a novel mechanism for endoscopic resection. Resection is performed by a rotary motion instead of the conventional linear motion. A novel resection loop and working element for controlling the movement of the resection loop allow the resection loop to move in clockwise and counterclockwise rotation. Embodiments include both monopolar and bipolar diathermy resectoscopes.

The resection capability of an exemplary rotatory resectoscope is significantly higher than that of a conventional resectoscope. The new design significantly increases the cutting loop size without need to increase the diameter of the resectoscope. The size of tissue chip that is resectable per single motion is much bigger than the size produced by a conventional loop. This results in benefits such as reduced operative time, reduced complications, and reduced anesthesia time.

BRIEF DESCRIPTION OF THE DRAWINGS

FIG. 1 is an exemplary rotary resectoscope.
FIG. 2 is a rotary resectoscope with internal components made visible.

DETAILED DESCRIPTION

Figure 3:
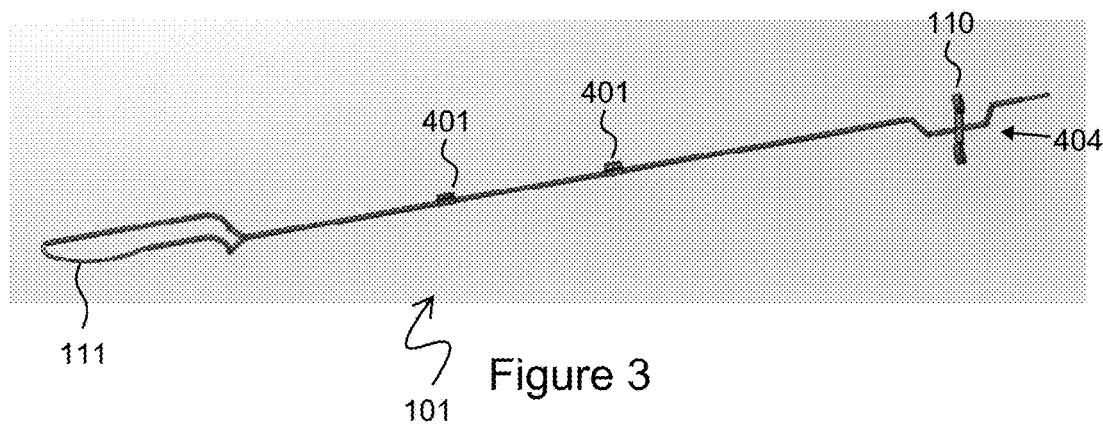
FIG. 3 is an exemplary loop of the rotary resectoscope.

FIG. 1 shows an exemplary resectoscope 100. A resectoscope is an endoscopic instrument used in surgeries of, for example, the bladder, prostate, uterus, urethra, or other target organ. To this end a resectoscope 100 may sometimes be referred to as a urological resectoscope. To access organs such as the bladder or prostrate, the instrument may be guided through and up the urethra following the body's natural pathway. This technique is minimally invasive and avoids the need for surgical incisions of a patient's skin and transcutaneous access. As a type of endoscopic instrument, one functionality of an exemplary resectoscope is visualization of the surgical site. A further functionality is the resection and extraction of tissue, such as for biopsy, removal of growths, and ablation of diseased or damaged tissue. For instance a resectoscope 100 may be used to resect prostrate or bladder lesions into small pieces of tissue under direct optical vision. Target lesions may be on the inner surfaces of the target organs.

Generally a resectoscope 100 includes at least the following parts: a loop 101, a telescope 104, and user controls 110. Additional elements depicted by FIG. 1 include a sheath 102 a handpiece 103. In a fully assembled state of a resectoscope 100, the loop 101 includes one or more electrodes 111 disposed at a distal end or distal tip of the instrument. The at least one electrode 111 protrudes or is protrudable from and retractable into a distal end of the sheath 102. The number of electrodes generally will be one or two depending on whether the loop 101 is configured to be monopolar or bipolar, both of which are compatible with the features of the invention. The user controls 110 are disposed at a proximal end of the instrument. For purposes of this disclosure, "distal" refers to a part further or furthest away from the surgeon (or other operator, typically a medical professional handling the instrument) whereas "proximal" refers to a part nearer or nearest to the surgeon.

Figure 9:
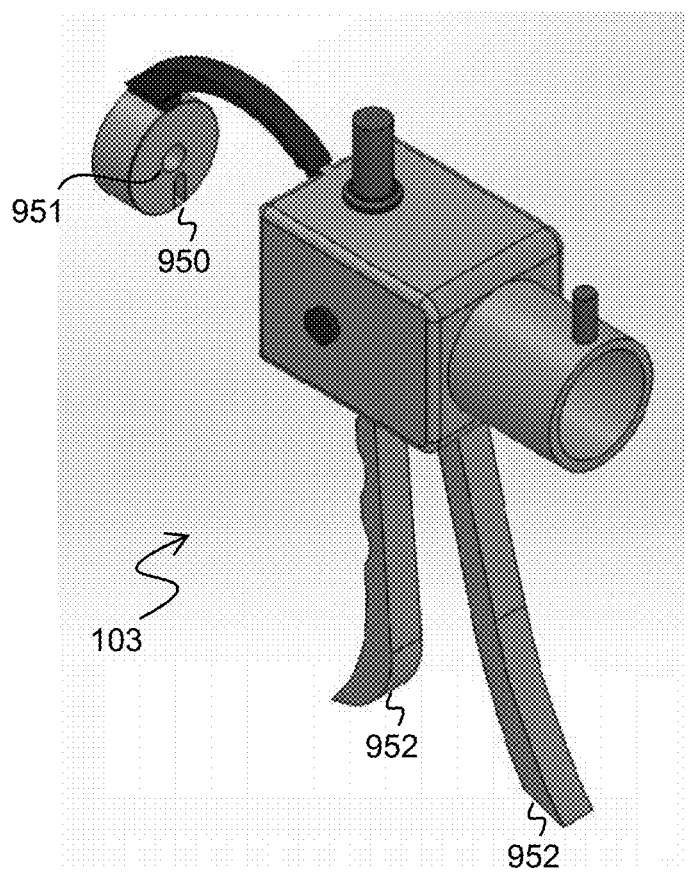
FIG. 9 is an exemplary handpiece of a rotary resectoscope.

The "user controls" may in fact consist of a single controller or multiple parts that are gripped, held, touched, tapped, swiped, slid, or otherwise contacted with the gloved hand of the surgeon. For purposes of this disclosure, the term "user controls" is treated as encompassing both singular and plural alternatives unless the context indicates otherwise. A more general term for any element which a user may control by direct contact is "working element" and "working elements". The term "working element" encompasses the handpiece 103, which is shown in FIG. 9, in addition to the user controls 110, which are entirely unique to the present invention.

The sheath 102 may include multiple subparts. In FIG. 1 an outerpart 102a is a metal cylinder whereas an inner part 102b, which is partly visible at the distal end of the instrument, is a thin plastic or ceramic cylinder which is non-conductive and fitted inside the outer cylinder. The sheath 102 may be alike or identical to known sheaths already common among existing resectoscopes. This is advantageous, with the novel features of the inventive device being backwards compatible with existing components of resectoscope systems. Generally speaking, a sheath 102 has a lumen from end to end through which other components are positioned when the resectoscope 100 is fully assembled. Both an irrigation fluid inlet 112 and an irrigation fluid outlet 113 may be arranged at a proximal end of the sheath.

FIG. 1 depicts a longitudinal axis 108 of the resectoscope 100. In a fully assembled state of resectoscope 100, longitudinal axis 108 describes the center longitudinal axis of the sheath 102 and of the telescope 104 (or at a minimum, the center longitudinal axis of these structures for their distal-most halves). Furthermore, the longitudinal axis 108 constitutes the axis of rotation about which the electrode 101 rotates, as will be discussed in greater detail below. To avoid obscuring the features of the drawing, FIG. 1 shows only a segment of the longitudinal axis 108, but the axis should be understood as extending the length of the figure.

FIG. 2 shows the resectoscope 100 rendered such that elements inside sheath 102 are visible. A few shape and size variations from FIG. 1 may be portrayed, but all elements are functionally consistent between FIGS. 1 and 2. The telescope 104 and loop 101 can be clearly seen running through the length of the sheath 102. The telescope 104 provides for the passage of light between a distal end of the resectoscope 100 and proximally positioned ports. The illustrated embodiment includes a port 109 for connection of an electrical cable and a port 114 to which a light source may be attached. The loop 101 has a distal cutting wire at the distal end of the resectoscope and a body passing through the length of the lumen of the sheath 102 to where user controls 110 are located at a proximal end of the instrument.

The user controls 110 of the resectoscope 100 are at a proximal end of the instrument and are usable to cause the at least one electrode 111 to rotate about the longitudinal center axis 108 of the telescope 104. The user controls 110 may comprise protrusions which extend outward, e.g. perpendicularly, from the longitudinal axis. The user controls 110 may further include rings or other ergonomic user interfaces which may be attached to or part of the protrusions. The user controls 110 may be tabs, handles, levers, or other configurations which allow for the application of a torque to induce the rotation of the loop 101 about the axis 108. The user controls 110 transmit movement from the user/operator (generally a surgeon) to the loop.

Figure 4:
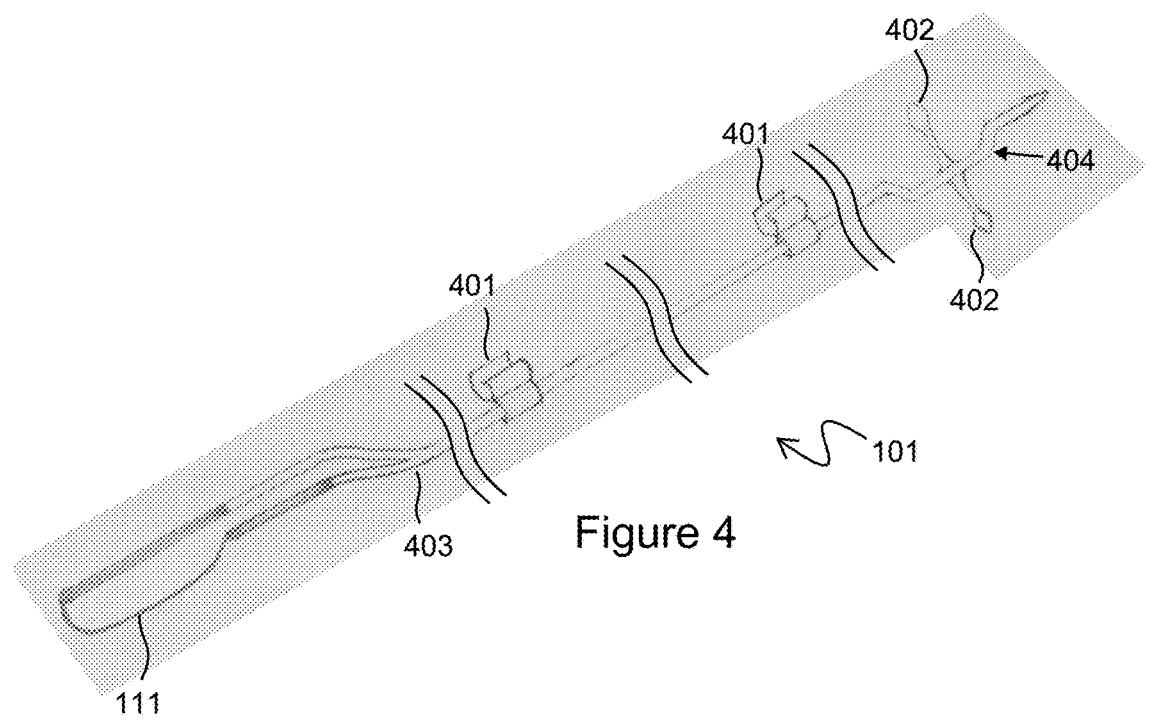
FIG. 4 is another depiction of the loop of the rotary resectoscope.

FIGS. 3 and 4 show a resectoscope loop 101. FIG. 3 shows the loop 101 from end to end, whereas FIG. 4 crops out three sections of wire to allow an enlarged view of the remaining illustrated elements. The loop 101 may be manufactured as a single piece as opposed to several parts, making the loop simple to fix and remove and more economically cost effective overall. The loop 101 comprises at least one electrode 111. The loop 101 comprises a plurality of electrodes in the case of a bipolar embodiment. In the illustrated example, the electrode 111 is configured as a long cutting wire. At least one or two couplers 401 are configured to couple the loop 101 with the telescope 104. The couplers 401 fix the radial separation of the loop 101 and telescope 104 to a constant value. A coupler 401 retains the loop 101 while permitting the loop 101 to rotate within the coupler 401 about the loop's own center longitudinal axis.

Conducting wires leading from either end of the electrode 111 spatially join/split at branch point 403. Between branch point 403 and the proximal end of the loop 101, the loop is configured substantially as a single cylindrical rod or pole which follows a linear axis. This portion of the loop is sometimes referred to as the body of the loop. The body of the loop 101 has a clear geometric deviation from the apparent linear axis at proximal region 404. The protrusions 402 are positioned in the deviation region 404. This deviation region 404 increases the spacing or gap between the protrusions 402 and the telescope in the resectoscope's fully assembled state. In addition, the deviation allows for an increase in the range of rotation of the loop.

Figure 5:
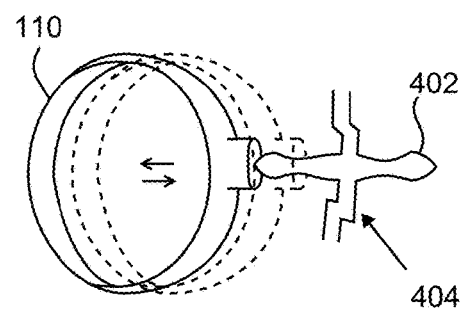
FIG. 5 is a magnified view of a proximal part of the loop.

FIG. 5 shows an enlarged view of the deviation region 404 and the protrusions 402 positioned there. The protrusions 402 generally have a fixed, static, permanent attachment with the remainder of the loop 101. Whereas the loop 101 is conductive, the protrusions 402 are preferably non-conductive. As discussed above, a variety of ergonomic user interfaces such as a ring may be removably attached to the protrusions 402. A ring advantageously is movable in a circular manner using an index finger. A single protrusion (with or without an accompanying user interface) may be sufficient in some embodiments for a user to exert a torque on the loop to bring about the desired rotation. Generally at least two protrusions on opposite sides of the loop are advantageous to enable use of the resectoscope either by the right hand or by the left hand, depending on the preference or handedness of the surgeon. User controls 110 may be further understood through the illustration of FIG. 6.

Figure 6:
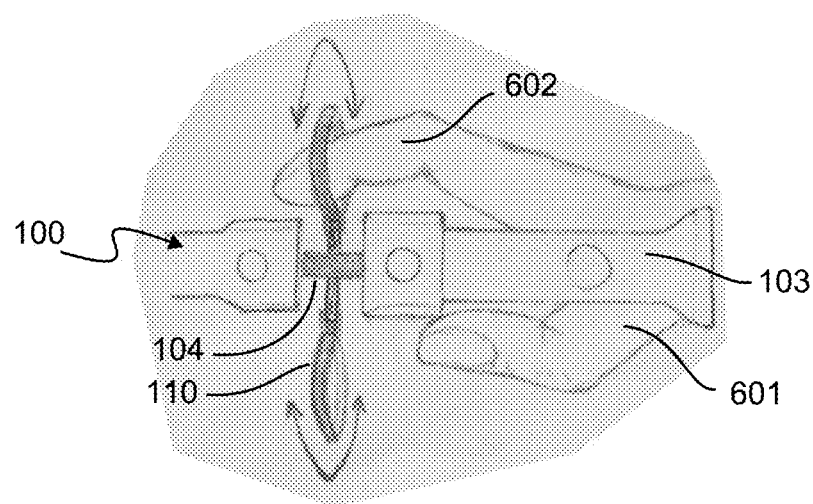
FIG. 6 is a top view of the proximal part of the rotary resectoscope shown held by an operator of the device.

FIG. 6 shows a top view of a proximal part of the resectoscope 100 as its being held by an operator's hand 601. The operator's index finger 602 is inside a ring connected to a protrusion of the loop. The user has the ability to move her finger 602 in a manner indicated by the arrows of FIG. 6. The handpiece 103 may be held by the operator as a user generally holds a gun. The "gun hold" hand placement is common among existing resectoscopes, and present embodiments advantageously do not disrupt this conventional grip already known and practiced among surgeons. The user controls 110 are positioned such that a user already gripping the handpiece 103 may simply slide her index finger 602 a small distance to the user controls 110 and control the desired rotation with little more than a small movement of the finger 602.

Figure 7:
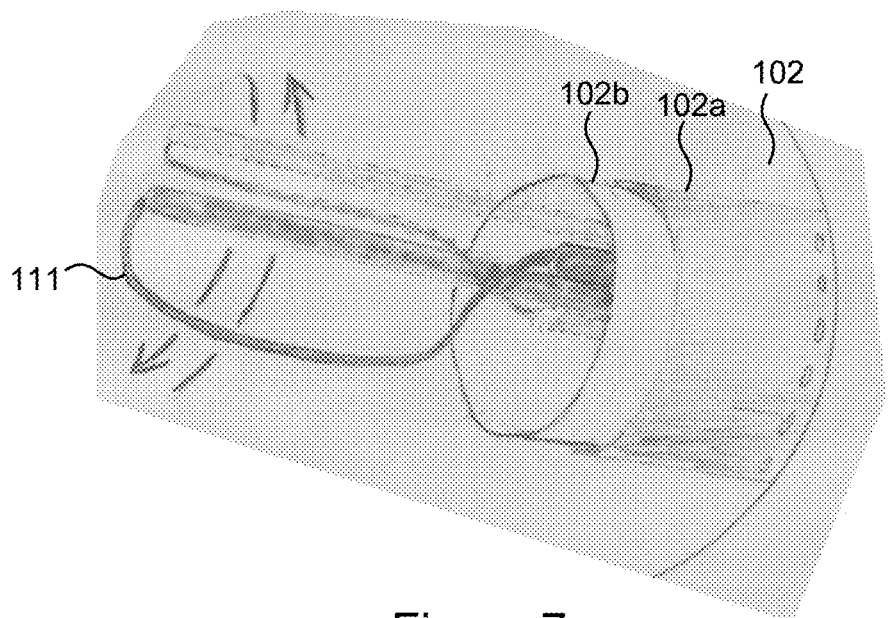
FIG. 7 is a magnified view of a distal part of the loop during a rotation.

Whereas FIG. 6 showed a proximal part of resectoscope actuated by the user, FIG. 7 illustrates the rotation of the electrode 111 at a distal part of the resectoscope resulting from the user's actuation. The arrows in FIG. 7 illustrate the path of the electrode as it rotates clockwise or counterclockwise about the center longitudinal axis 108 of the telescope. The telescope is not visible in FIG. 7 since its end is a few millimeters behind the end of the sheath. The dotted lines show a different position of the loop to contrast with the position shown by the solid lines.

Figure 10A:
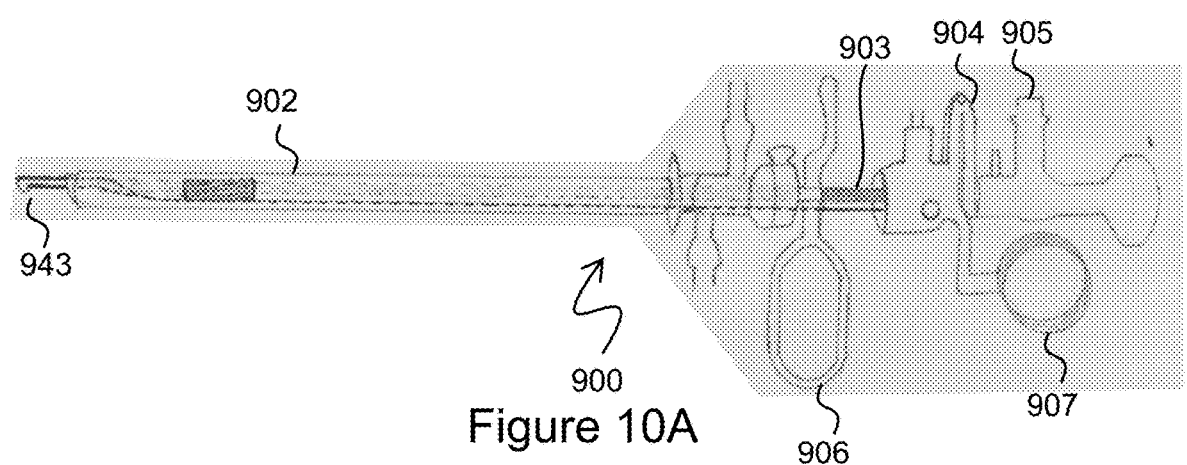
FIG. 10A is a resectoscope mechanically actuated with a conventional linear motion.
Figure 10B:
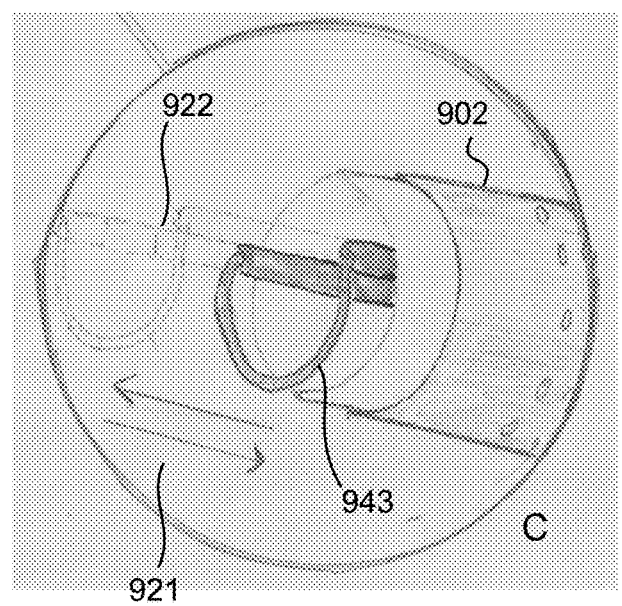
FIG. 10B is an enlarged view of the distal tip of the resectoscope of FIG. 10A.
Figure 10C:
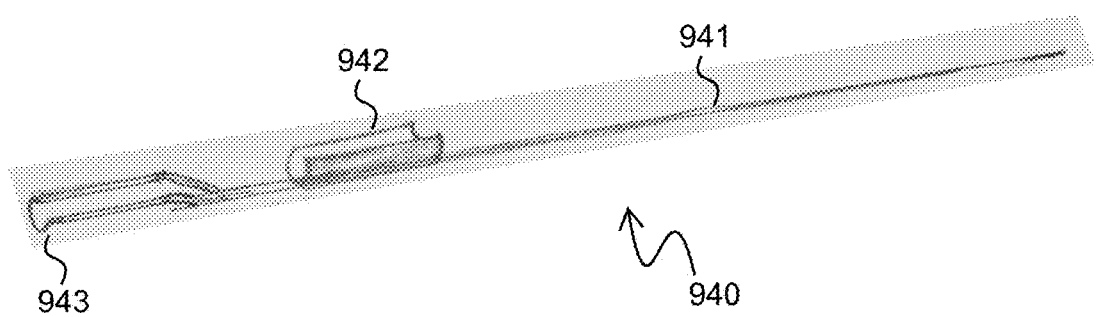
FIG. 10C is the electrode assembly of the resectoscope of FIG. 10A.

All or a substantial part of the area enclosed by the loop in the region of the electrode 111 may lie in a geometric plane corresponding with (e.g., parallel to) the longitudinal direction of the instrument. (By way of contrast, the resectoscope 900 in FIG. 10A has a loop and electrode which form a cross sectional area perpendicular to the longitudinal direction of the instrument.) Because of the loop's cutting electrode orientation with respect to the longitudinal axis of the instrument, the geometric area generally defined by the loop in the region of the electrode may exceed the cross-sectional area of the sheath and yet still be retractable into and extendable from the sheath.

As already indicated, the actuation mechanism of the resectoscope 100 uses a rotary (e.g., rotatory, arcuate, circular) movement from the user controls that makes the movement of the electrode very accurate and more controlled; the cutting loop at the distal end will move with the same amount of movement applied by the surgeons' finger. In other words, the user controls are configured such that a rotation of the user controls through a first angle of rotation causes a rotation of the at least one electrode through a second angle of rotation, wherein the first angle and second angle are equal. This contrasts with the use of a drive screw mechanism to convert linear actuation by the user into rotational motion of the loop. A conversion of linear displacement to rotational displacement would make control of the electrode and performance of a procedure more difficult. Along the same lines, a drive screw may be suited for rapid rotation of an electrode but less suitable for careful controlled rotation as provided with the exemplary embodiments described herein. Generally speaking, an exemplary resectoscope 100 is not operated, or even necessarily operable, with rapid rotation (e.g., a rotational speed exceeding the maximum rate at which an average adult human can rotate or move a finger or hand). The present actuation is generally hand driven (e.g., as opposed to motor-driven).

Figure 8A:
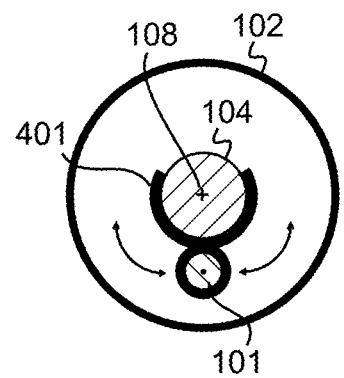
FIG. 8A shows a cross-sectional plane taken from Section A-A in FIG. 2.
Figure 8B:
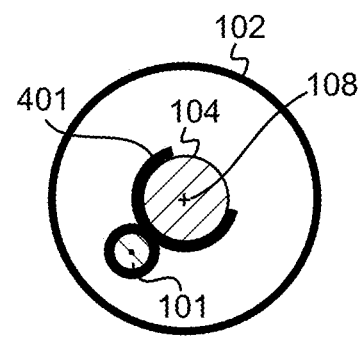
FIG. 8B shows the cross-sectional view from FIG. 8A after the loop has been rotated clockwise.
Figure 8C:
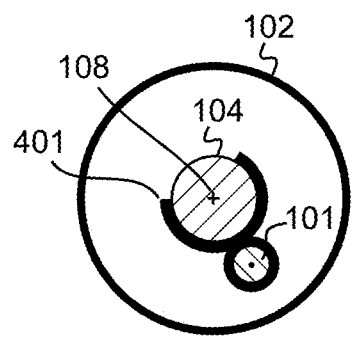
FIG. 8C shows the cross-sectional view from FIG. 8A after the loop has been rotated counterclockwise.

FIG. 8A shows a cross-sectional plane taken from resectoscope 100 at line A-A in FIG. 2. Note that for simplicity and clarity of illustration, the proportions of some elements is not necessarily accurately portrayed, and any interior details of either the telescope 104 or the loop 101 are omitted and represented instead with basic hatching. Both the telescope 104 and the loop 101 are positioned within the lumen of the sheath 102. The center longitudinal axis 108 is the center longitudinal axis of both the sheath 102 and the telescope 104. However, it is possible that in some embodiments the sheath has a different axis from the telescope. The coupler 401 connects the telescope 104 with the loop 101 such that the center of each structure maintains a fixed distance with respect to the other center. Despite this fixed spatial parameter, the loop 101 is free to rotate about the center longitudinal axis 108 of the telescope 104 as indicated by the arrows in FIG. 8A. The rotation may be clockwise or counterclockwise. FIG. 8B shows roughly a 45 degree rotation in a clockwise direction starting from the position depicted by FIG. 8A. FIG. 8C shows roughly a 45 degree rotation in a counterclockwise direction starting from the position depicted by FIG. 8A.

The arrangement of components as depicted in FIG. 8A is significant to ensuring use of the electrode under direct visualization by the surgeon (e.g., as opposed to blind cutting). The design of the distal part of the cutting loop in the resection loop makes the cutting wire rotate around the same center longitudinal axis 108 of the telescope 104. That means the loop will be kept all the time in the center of the surgeon's field of vision. If the axis of rotation were parallel to but not the same central longitudinal axis as the telescope, certain positions during the motion of cutting loop would be very peripheral and may even disappear from the field of vision. This a significant point, because the field of vision of telescopes is tubular, so things that are lateral to the telescope might not be seen.

FIG. 9 shows an exemplary handpiece 103 for the rotary resectoscope 100. In many respects, the handpiece 103 may resemble and share a number of features with known resectoscope handpieces already on the market. For instance the handles 952 may be positioned on an underside of the handpiece 103. Contrary to conventional handpieces, the handles 952 may have completely fixed positions in relation to one another and the remainder of the handpiece. A hole or guide channel 951 is provided to retain and support a telescope's tube. Exemplary devices may use conventional telescopes, as well. A key distinction of handpiece 103, however, is hole or slot 950 provided adjacent and in this case below the guide channel 951. The hole or slot 950 is configured to position and retain the unique loop according to this disclosure, as depicted by FIGS. 1 and 2. In addition the handles 952 may be thin to reduce the weight of the overall instrument.

Materials for components of exemplary resectoscopes described herein may conform to existing material selections for existing resectoscopes. In this way manufacturability and FDA approval, where necessary, may be readily facilitated. Exemplary materials for the components include but are not limited to stainless steel, aluminum, thermoplastic polymers like acetal resins or polyoxymethylene (e.g., Delrin®), and other materials suited for and permitted in surgical instruments.

Funding Statement:

This technology was funded by Science and Technology Unit-King Abdulaziz University-Kingdom of Saudi Arabia-award number (UE-41-108).

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of a "negative" limitation or use of such exclusive terminology as "solely," "only" and the like in connection with the recitation of claim elements.

While exemplary embodiments of the present invention have been disclosed herein, one skilled in the art will recognize that various changes and modifications may be made without departing from the scope of the invention as defined by the following claims.

What is claimed is:

1. A resectoscope with a proximal end and a distal end, comprising:
   a telescope with a longitudinal center axis;
   a loop with at least one electrode at the distal end; and
   user controls at the proximal end that are rotatable,
   wherein rotation of the user controls while the telescope is stationary causes the at least one electrode to rotate relative to the telescope around a first axis of rotation, wherein the user controls are configured to be directly contacted by a user to cause the at least one electrode to rotate, and wherein the user controls are rotatable around a second axis of rotation, wherein the second axis of rotation is the longitudinal center axis of the telescope.

2. The resectoscope of claim 1, wherein the user controls are configured such that a rotation of the user controls through a first angle of rotation causes a rotation of the at least one electrode through a second angle of rotation, wherein the first angle and second angle are equal.

3. The resectoscope of claim 1, wherein the user controls comprise one or more protrusions from the loop which extend perpendicularly with respect to the longitudinal center axis and which are rotatable about the longitudinal center axis.

4. The resectoscope of claim 3, wherein the user controls further comprise one or more rings each removably attachable directly to one of the one or more protrusions and sized to permit finger placement inside.

5. The resectoscope of claim 1, wherein the loop comprises an elongate support body, wherein the elongate support body comprises a deviation region, wherein the user controls are positioned in the deviation region of the loop such that the user controls are spaced further apart from the telescope than is a remainder of the loop.

6. The resectoscope of claim 1, further comprising one or more couplers which couple the loop to the telescope.

7. The resectoscope of claim 6, wherein the one or more couplers fix the radial separation distance of the loop and telescope to a constant value.

8. The resectoscope of claim 1, further comprising a sheath.

9. The resectoscope of claim 1, wherein the loop is monopolar or bipolar.

10. The resectoscope of claim 1, wherein the first axis of rotation is the longitudinal center axis of the telescope.

11. A resectoscope with a proximal end and a distal end, comprising:

a telescope with a longitudinal center axis;

a loop comprising an elongate support body and at least one electrode at the distal end;

one or more couplers configured to couple the loop to the telescope while permitting the elongate support body to rotate around the telescope while the telescope is stationary; and user controls at the proximal end that are rotatable, wherein rotation of the user controls while the telescope is stationary causes the elongate support body to rotate around the telescope, wherein an axis of rotation of the elongate support body is the longitudinal center axis of the telescope.

12. The resectoscope of claim 11, wherein the one or more couplers fix a radial separation distance of the loop and telescope to a constant value.

* * * * *